(12) United States Patent
Vanney

(10) Patent No.: US 6,406,491 B1
(45) Date of Patent: Jun. 18, 2002

(54) COMPLIANT TRANSMYOCARDIAL IMPLANT

(75) Inventor: Guy P. Vanney, Blaine, MN (US)

(73) Assignee: HeartStent Corporation, St. Paul, MN (US)

( * ) Notice: Subject to any disclaimer, the term of this patent is extended or adjusted under 35 U.S.C. 154(b) by 0 days.

(21) Appl. No.: 09/304,650

(22) Filed: May 4, 1999

(51) Int. Cl.$^7$ .................................................. A61F 2/06
(52) U.S. Cl. ...................... 623/1.3; 623/1.12; 623/1.36; 604/8
(58) Field of Search ............................... 623/1.12, 1.13, 623/1.14, 1.3, 1.15, 1.23, 12, 1.36; 606/191, 198; 128/898; 604/8

(56) References Cited

U.S. PATENT DOCUMENTS

| | | |
|---|---|---|
| 4,300,244 A | 11/1981 | Bokros |
| 5,755,682 A | 5/1998 | Knudson et al. |
| 6,053,942 A | 4/2000 | Eno et al. |

FOREIGN PATENT DOCUMENTS

| | | |
|---|---|---|
| WO | WO 98/06356 | 2/1998 |
| WO | WO 98/46115 | 10/1998 |
| WO | WO 99/40868 | 8/1999 |

*Primary Examiner*—Dinh X. Nguyen
(74) *Attorney, Agent, or Firm*—Merchant & Gould P.C.

(57) ABSTRACT

A transmyocardial implant includes a hollow rigid conduit having a vessel portion and a myocardial portion. The vessel portion is sized to be inserted into a coronary vessel. The myocardial portion is sized to extend from the vessel portion and through a myocardium into a heart chamber. The conduit has open vessel and myocardial ends on respective ones of the vessel and myocardial portions to define a blood flow pathway within an interior of the conduit between the vessel and myocardial ends. The myocardial portion is formed of a conduit material sufficiently rigid to resist deformation and closure of the pathway in response to contraction of the myocardium. The vessel portion has a radial compliance approximating a radial compliance of the vessel.

9 Claims, 2 Drawing Sheets

COMPLIANT TRANSMYOCARDIAL IMPLANT

BACKGROUND OF THE INVENTION

1. Field of the Invention

This invention pertains to an implant for passing blood flow directly between a chamber of the heart and a coronary vessel. More particularly, this invention pertains to such an implant with an enhanced design for enhanced compliance of a transmyocardial conduit in a coronary vessel.

2. Description of the Prior Art

Commonly assigned U.S. Pat. No. 5,755,682 and PCT International Publication No. WO 98/06356 teach an implant for defining a blood flow conduit directly from a chamber of the heart to a lumen of a coronary vessel. An embodiment disclosed in the aforementioned patent and application teaches an L-shaped implant. The implant is a conduit having one leg sized to be received within a lumen of a coronary artery and a second leg sized to pass through the myocardium and extend into the left ventricle of the heart. As disclosed in the above-referenced patent and application, the conduit remains open for blood flow to pass through the conduit during both systole and diastole. The conduit penetrates into the left ventricle in order to prevent tissue growth and occlusions over an opening of the conduit. 08/944,313 filed Oct. 6, 1997, entitled "Transmyocardial Implant", and filed in the name of inventors Katherine S. Tweden, Guy P. Vanney and Thomas L. Odland, teaches an implant such as that shown in the aforementioned '682 patent with an enhanced fixation structure. The enhanced fixation structure includes a fabric surrounding at least a portion of the conduit to facilitate tissue growth on the exterior of the implant. This application has the same disclosure as PCT/US 98/17310.

Implants such as those shown in the aforementioned patent and applications include a portion to be placed within a coronary vessel and a portion to be placed within the myocardium. When placing a portion of the implant in the coronary vessel, the vessel is incised a length sufficient to insert the implant. When placed within the coronary vessel, the implant discharges flow axially into the vessel.

When placing an implant, a portion of the coronary artery is dissected. The dissected portion is incised and the vessel portion of the implant is inserted into the lumen. A stay suture secures the artery to the implant. The stay suture is paced around the artery and vessel portion a distanced spaced from the open end of the vessel portion.

The implant is rigid. The vessel is compliant. Since the vessel is radially flexing over time, the compliance mismatch between the vessel portion and the vessel may damage the vessel.

SUMMARY OF THE INVENTION

According to a preferred embodiment of the present invention, a transmyocardial implant is disclosed for establishing a blood flow path through a myocardium between a heart chamber and a lumen of a coronary vessel. The implant includes a hollow rigid conduit having a vessel portion and a myocardial portion. The vessel portion is sized to be inserted into the vessel. The myocardial portion is sized to extend from the vessel portion and through the myocardium into the chamber. The conduit has open vessel and myocardial ends on respective ones of the vessel and myocardial portions to define a blood flow pathway within an interior of the conduit between the vessel and myocardial ends. The myocardial portion is formed of a conduit material sufficiently rigid to resist deformation and closure of the pathway in response to contraction of the myocardium.

The vessel portion has a radial compliance approximating a radial compliance of the vessel.

DESCRIPTION OF THE PREFERRED EMBODIMENT

Figure 1:
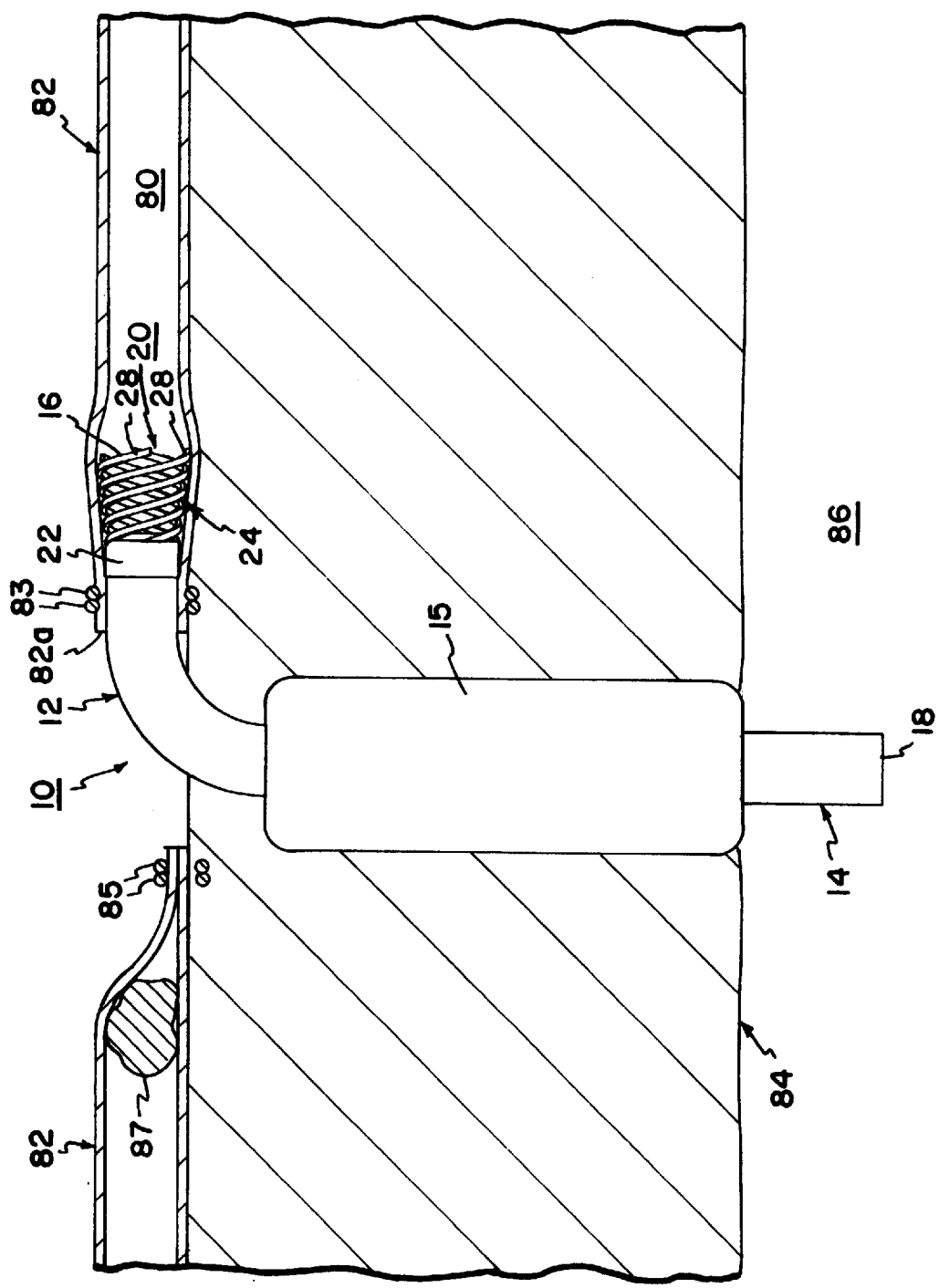
FIG. 1 is a side elevation view of a transmyocardial conduit according to the present invention and showing a myocardial portion of the implant placed through a heart wall and with a vessel portion placed in a coronary vessel.

With initial reference to FIG. 1, a transmyocardial conduit 10 is shown in the form of an L-shaped rigid tube. In the preferred embodiment described below, the conduit 10 is titanium but may be any other rigid biocompatible material such as pyrolytic carbon or may be titanium coated with pyrolytic carbon. The material of the conduit 10 is preferably a rigid material in order to withstand contraction forces of the myocardium. By way of example, the tube will have an outside diameter of about 2.5 millimeters and an internal diameter of about 2.0 millimeters to provide a wall thickness of about 0.25 millimeters.

The conduit 10 has a first or vessel portion 12 sized to be received within the lumen of a coronary vessel such as the lumen 80 of a coronary artery 82. The conduit has a second or myocardial portion 14 extending at an angle to the axis of portion 12.

The myocardial portion 14 is sized to extend from the coronary artery 82 directly through the myocardium (heart wall) 84 and protrude into the left ventricle 86 of a patient's heart.

The vessel portion 12 has a vessel opening 16. The myocardial portion 14 has a myocardial opening 18 in communication with an interior 19 (shown in FIG. 2) of the implant 10. Therefore, blood can freely flow through the conduit 10 between the left ventricle 86 and the lumen 80 of the coronary artery 82. Blood flows axially out of opening 16 parallel with the axis of lumen 80.

As discussed more fully in the afore-mentioned commonly assigned and co-pending U.S. Patent application Ser. No. 08/944,313, the myocardial portion 14 may be provided with a tissue-growth inducing material such as a polyester sleeve 15 to immobilize the implant 10 within the myocardium 84.

Figure 2:
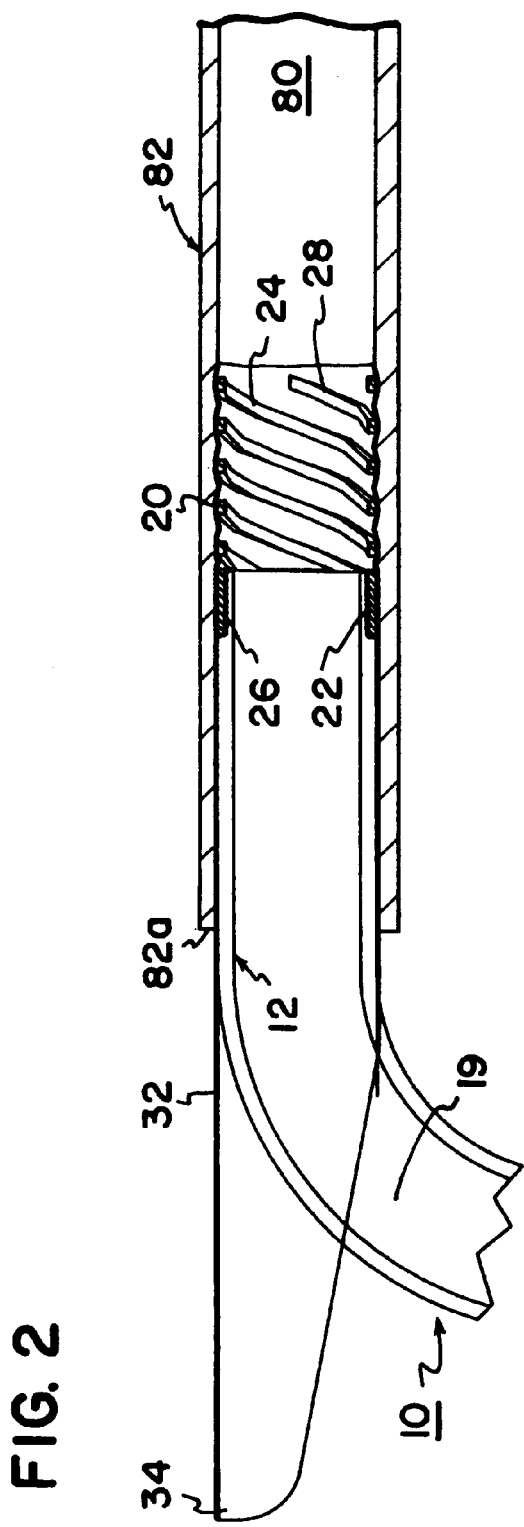
FIG. 2 is a side sectional view of a vessel portion of the conduit of FIG. 1 placed in a coronary vessel with a coiled end of the vessel portion held in a constricted state.

At least a distal portion of the vessel portion 12 is a compliant structure 20. In the embodiment shown, the compliant structure 20 includes a tubular member 22 connected to a radially flexible coil 24. As shown in FIG. 2, the vessel portion 12 includes an annular groove 26. The tubular member 22 slips or is press-fit into the groove 26.

The coil 24 is preferably four individual coils 28 extending from the tubular member in a cantilevered fashion at 90° spacings about the circumference of the tubular member 22. The individual coils 28 expand for the coil 24 to assume a conical shape (shown in FIG. 1) with a narrow end at the tubular member 22. At the opening 16, the coil 24 expands to a diameter about 0.75 mm larger than the coil's narrow diameter.

Alternatives to coils 28 include axially extending fingers which expand radially outwardly and lattice structured stents.

To facilitate placement in a vessel 82, a sleeve 32 of thin tear-away plastic with a handle 34 surrounds the coil 24. The sleeve 32 compresses the coil 24 from the conical shape of FIG. 1 to a cylindrical shape illustrated in FIG. 2.

A surgeon dissects a portion of the artery 82 away from the myocardium 84.

The surgeon ligates the artery 82 distal to an obstruction 87 with sutures 85. The surgeon then forms an incision through the artery 82 distal to the ligating suture 85.

The coil 24 (compressed by sleeve 32) is slipped into the lumen 80 through the open end 82a of the artery 82. A stay suture 83 is placed around the vessel 82 over the vessel portion 12. A surgical procedure for placing an implant and tools for such procedure are more fully described in commonly assigned and co-pending U.S. patent application Ser. No. 09/179,711 filed Oct. 27, 1998.

After positioning the implant as shown in FIG. 2, the sleeve 32 is peeled away by pulling on handle 34 permitting the coil 24 to expand. The expansion causes a corresponding expansion of the lumen 80 at the incised artery end 82a (FIG. 1). The amount of enlargement of the artery 82 is a function of the natural swelling of the artery. More specifically, the coil 24 is flexible and is radially compressible to compress and expand in response to compression and expansion of the artery 82. Accordingly, the compliance of the vessel portion 12 now more closely matches a compliance of the artery. The compliance matching is achieved by material selection and geometry of the individual coils 28 for the coil 24 to have a compliance approximating arterial compliance. Such compliance is about $10 \times 10^{-2}\%$ radial change per 1 mmHg.

From the foregoing, the invention has been described in a preferred embodiment. Modifications and equivalents of the disclosed concepts are intended to be included within the scope of the claims.

What is claimed is:

1. A transmyocardial implant for establishing a blood flow path through a myocardium between a heart chamber and a lumen of a coronary vessel, said implant comprising:

a hollow rigid conduit having a vessel portion and a myocardial portion, said vessel portion sized to be inserted into said vessel, said myocardial portion sized to extend from the vessel portion and through said myocardium into said chamber;

said conduit having open vessel and myocardial ends on respective ones of said vessel and myocardial portions to define a blood flow pathway within an interior of said conduit between said vessel and myocardial ends;

said myocardial portion of said conduit formed of a conduit material sufficiently rigid to resist deformation and closure of said pathway in response to contraction of said myocardium;

at least a portion of said vessel portion having a radial compliance approximating a radial compliance of said vessel.

2. An implant according to claim 1 wherein said portion of said vessel portion is an open construction flexible member.

3. An implant according to claim 1 wherein said portion of said vessel portion is radially compressible.

4. An implant according to claim 1, further comprising a delivery system, the delivery system comprising a removable sleeve for holding said portion of said vessel portion in a radially compressed state until after placement of said vessel portion in said artery with said sleeve removable thereafter for said vessel portion to radially expand and contract in response to expansion and contraction of said vessel.

5. An implant according to claim 1 wherein said portion of said vessel portion is a coil.

6. An implant according to claim 1, wherein said portion of said vessel portion has a radial compliance of about $10 \times 10^{-2}\%$ radial change per 1 mmHg.

7. A transmyocardial implant system for establishing a blood flow path through a myocardium between a heart chamber and a lumen of a coronary vessel, said system comprising:

a hollow rigid conduit having a vessel portion and a myocardial portion, said vessel portion sized to be inserted into said vessel, said myocardial portion sized to extend from the vessel portion and through said myocardium into said chamber;

said conduit having open vessel and myocardial ends on respective ones of said vessel and myocardial portions to define a blood flow pathway within an interior of said conduit between said vessel and myocardial ends;

said myocardial portion of said conduit formed of a conduit material sufficiently rigid to resist deformation and closure of said pathway in response to contraction of said myocardium;

a compressible portion connected to said open vessel end, said compressible portion having radial compliance approximately the radial compliance of said vessel; and a removable sleeve positioned about said compressible portion and holding said compressible portion in a radially compressed state wherein the compressible portion in the compressed state is sized to be inserted into said vessel.

8. A method of establishing a blood flow path through a myocardium between a heart chamber and a lumen of a coronary vessel, the method comprising the steps of:

providing an implant comprising a hollow rigid conduit having a vessel portion and a myocardial portion, said vessel portion sized to be inserted into said vessel, said myocardial portion sized to extend from the vessel portion and through said myocardium into said chamber, said implant having open vessel and myocardial ends on respective ones of said vessel and myocardial portions to define a blood flow pathway within an interior of said conduit between said vessel and myocardial ends, and a compressible portion connected to said open vessel end, said compressible portion having radial compliance approximately the radial compliance of said vessel;

placing said myocardium portion into said myocardium and inserting said vessel portion and said compressible portion into said coronary vessel.

9. A method according to claim 8, the method further comprising the step of securing said vessel about said vessel portion and said compressible portion with a stay suture about said vessel over only said vessel portion.

* * * * *